United States Patent
Kim et al.

(10) Patent No.: US 11,246,885 B2
(45) Date of Patent: Feb. 15, 2022

(54) KELOID PREVENTION OR TREATMENT METHOD USING LIQUID PHASE PLASMA

(71) Applicant: AJOU UNIVERSITY INDUSTRY-ACADEMIC COOPERATION FOUNDATION, Gyeonggi-do (KR)

(72) Inventors: Chul Ho Kim, Seoul (KR); Sung Un Kang, Gyeonggi-do (KR)

(73) Assignee: AJOU UNIVERSITY INDUSTRY-ACADEMIC COOPERATION FOUNDATION, Gyeonggi-do (KR)

( * ) Notice: Subject to any disclaimer, the term of this patent is extended or adjusted under 35 U.S.C. 154(b) by 0 days.

(21) Appl. No.: 16/643,418

(22) PCT Filed: Aug. 23, 2018

(86) PCT No.: PCT/KR2018/009700
§ 371 (c)(1),
(2) Date: Feb. 28, 2020

(87) PCT Pub. No.: WO2019/045360
PCT Pub. Date: Mar. 7, 2019

(65) Prior Publication Data
US 2020/0254008 A1    Aug. 13, 2020

(30) Foreign Application Priority Data
Aug. 31, 2017  (KR) .......... 10-2017-0110764

(51) Int. Cl.
*A61K 33/00* (2006.01)
*A61P 17/02* (2006.01)

(52) U.S. Cl.
CPC .............. *A61K 33/00* (2013.01); *A61P 17/02* (2018.01)

(58) Field of Classification Search
CPC ............................. A61K 33/00; A61P 17/02
See application file for complete search history.

(56) References Cited

U.S. PATENT DOCUMENTS

| | | | |
|---|---|---|---|
| 5,876,663 A * | 3/1999 | Laroussi | ......... A23L 3/005 204/164 |
| 6,518,538 B2 | 2/2003 | Bernabei | |
| 9,226,790 B2 | 1/2016 | Zemel et al. | |
| 2007/0213700 A1 | 9/2007 | Davidson et al. | |
| 2008/0119781 A1* | 5/2008 | King | ......... A61P 17/02 604/22 |
| 2012/0089084 A1 | 4/2012 | O'Keeffe et al. | |
| 2013/0345620 A1 | 12/2013 | Zemel et al. | |
| 2016/0296763 A1 | 10/2016 | Kim et al. | |
| 2020/0129386 A1 | 4/2020 | Kim et al. | |

FOREIGN PATENT DOCUMENTS

| | | |
|---|---|---|
| JP | 10-286316 | 10/1998 |
| JP | 2014-212839 | 11/2014 |
| KR | 10-0509848 | 4/2004 |
| KR | 10-0479741 | 3/2005 |
| KR | 10-1101321 | 5/2010 |
| KR | 20120039199 A | 4/2012 |
| KR | 10-1568380 | 11/2015 |
| KR | 10-1635718 | 7/2016 |
| KR | 101657063 B1 | 9/2016 |
| WO | WO 2015/191843 | 12/2015 |
| WO | WO 2016/167516 | 10/2016 |

OTHER PUBLICATIONS

Sharma, Effects of Cold Atmospheric Pressure Plasma Jet on the Viability of Bacillus subtilis Endospores, 2013, gair.media.gunma-u.ac.jp/dspace/bitstream/10087/7661/1/Thesis%20for%20Doctor%20of%20Engineering%20(VinitaSharma).pdf (Year: 2013).*
Kubinova et al., "Non-thermal Air Plasma Promotes the Healing of Acute Skin Wounds in Rats," Sci Rep (2017) 7: 45183, 11 pages.
Lee et al., "Suppression of scar formation in a murine A23burn wound model by the application of non-thermal plasma," Appl. Phys. Lett. (2011) 99: 203701.
Sato et al., "Successful Use of Argon Plasma Coagulation and Tranilast to Treat Granulation Tissue Obstructing the Airway After Tracheal Anastomosis," Chest (2000) 118 (6), 1829-1831.
Kang et al., "N2 non-thermal atmospheric pressure plasma promotes wound healing in vitro and in vivo: Potential modulation of adhesion molecules and matrix metalloproteinase-9." Experimental Dermatology (2017) 26:163-170.
Lee et al., "Nonthermal Plasma Induces Apoptosis in ATC Cells: Involvement of JNK and p38 MAPK-Dependent ROS," Yonsei Med J (2014) 55(6):1640-1647.

* cited by examiner

*Primary Examiner* — Ali Soroush
(74) *Attorney, Agent, or Firm* — Morrison Foerster LLP

(57) ABSTRACT

The present invention relates to a method of preventing or treating keloids using a liquid plasma. A liquid plasma according to the present invention is remarkably effective in inhibiting the generation and proliferation of keloids, thus being expected to be greatly utilized for the prevention and treatment of keloids.

5 Claims, 3 Drawing Sheets

KELOID PREVENTION OR TREATMENT METHOD USING LIQUID PHASE PLASMA

STATEMENT OF GOVERNMENTAL SUPPORT

The invention was supported by the Ministry of Health and Welfare (No. HR21C1003 (1465034377)) and the Ministry of Science and ICT(MSIT) (No. 1711052530 (2015R1A2A1A01002968)) and the Ministry of Science and ICT(MSIT) (No. 1711044743 (2012M3A9B2052870)) and the Ministry of Science and ICT(MSIT) (No. 1711058433 (2011- 0030043)) (Republic of Korea).

CROSS REFERENCE TO RELATED APPLICATIONS

This application is a National Stage application under 35 U.S.C. § 371 of International Application No. PCT/KR2018/009700 filed on Aug. 23, 2018, which claims priority to Korean application No. 10-2017-0110764, filed Aug. 31, 2017, the contents of which are hereby incorporated by reference in their entirety.

TECHNICAL FIELD

The present invention relates to a method of preventing or treating keloids using a liquid plasma.

BACKGROUND ART

Keloid, which refers to a disease wherein fibrous tissues abnormally, densely grow during wound healing after skin damage, has a property of spreading to surrounding areas beyond the size of a wound or an inflamed area. Clinically, cases wherein the epidermis is normal, but the dermis is proliferated, thus being thick and vessel-rich, and infiltration of inflammatory cells increases compared to normal scar tissues are diagnosed as keloid. Collagen bundles in normal dermis are relaxed and distorted, whereas collagen bundles in keloids are thick and dense. Histologically, keloid results in large, broad, closely-aligned collagen fibers consisting of numerous fibrils, and thick and hyalinized collagen that is irregularly arranged in a spiral shape is called keloid collagen. Since such keloid wildly proliferates, it may cause cosmetic problems and, when generated at important areas such as joints, may obstruct joint function. Therefore, it is most important for people with the potential for keloids to avoid injury. Until now, there is no way to prevent for inevitably occurred wounds from proceeding to keloids, so there is an urgent need for development thereof.

Plasma, which is an ionized gas that satisfies the Debye sheath in physics or chemistry, is an aggregate of charged particles having electrical conductivity. A liquid plasma refers to a liquid material treated with the plasma. As attempts to apply plasma to the biomedical field, technologies such as "SKIN TREATMENT APPARATUS USING PLASMA (KR 10-1568380 B1)", "METHOD OF TREATING SKIN WITH PLASMA (U.S. Pat. No. 9,226,790 B2)", and "PLASMA APPARATUS FOR SKIN SURFACE MODIFICATION (U.S. Pat. No. 6,518,538 B2)" have been recently developed. However, there is no technology development regarding the treatment of keloids in the form of liquid plasma.

Therefore, the present invention is related to a method of preventing or treating keloids using a liquid plasma, and a liquid plasma of the present invention is remarkably effective in inhibiting the generation and proliferation of keloids, thus being expected to be greatly utilized for the prevention and treatment of keloids.

DISCLOSURE

Technical Problem

Therefore, the present invention has been made in view of the above problems, and it is one object of the present invention to provide a method of preventing or treating keloids using a liquid plasma.

It will be understood that technical problems of the present invention are not limited to the aforementioned problems and other technical problems not referred to herein will be clearly understood by those skilled in the art from disclosures below.

Technical Solution

Hereinafter, various embodiments described herein will be described with reference to the accompanying drawings. In the following description, for complete understanding of the present invention, various specific details, e.g., such as specific forms, compositions, processes, and the like, are described. However, certain embodiments may be implemented without one or more of these specific details or with other known methods and forms. In other embodiments, well-known process and manufacturing techniques are not described in specific forms, in order not to unnecessarily obscure the present invention. References throughout the specification for "one embodiment" or "an embodiment" mean that particular features, forms, compositions, or characteristics disclosed in connection with the embodiment are included in one or more embodiments of the present invention. Accordingly, "one embodiment" or "an embodiment" expressed in various parts throughout this specification does not necessarily represent the same embodiment of the present invention. Additionally, particular features, forms, compositions, or characteristics may be combined in any suitable manner in one or more embodiments.

In the present specification, "keloid" is a disease wherein fibrous tissues abnormally, densely grow during wound healing after skin damage, and is also called "benign dermal fibrous tumor". Keloid is caused by impairment in a function of properly regulating and inhibiting a wound healing process, is thought to be caused by abnormal accumulation of extracellular matrix (ECM) such as excessive secretion of collagen, and does not become malignant. Unlike normal scars, keloids are hard, protrude above the skin surface, and have red and irregular surfaces. Since keloids widely spread, they can cause cosmetic problems when occur on the face, and can cause movement disorders when occurring at important areas such as joints.

Keloids can infiltrate surrounding normal skin beyond an original wound unlike hypertrophic scars. Accordingly, it is necessary to distinguish keloids from hypertrophic scars. More particularly, keloids occur months after trauma, do not improve over time, spread to surrounding areas beyond an original lesion site, occur only in people with genetic factors, and occur in people with dark skin, whereas hypertrophic scars occur quickly after trauma, improve over time, are confined to wound sites, more frequently occur, and are not related to skin color.

In an embodiment of the present invention, "non-thermal atmospheric pressure plasma" is also referred to as cold or non-equilibrium plasma and is a concept opposite to thermal plasma. Non-thermal atmospheric pressure plasma can be easily produced with low energy under relatively low pressure. In the case of non-thermal atmospheric pressure plasma, the temperature of reaction gas is similar to that of the atmosphere, but electron temperature is about 10 to 100 times higher than the atmosphere temperature. Non-thermal atmospheric pressure plasma generates chemically highly reactive reactants at normal and high pressures, and thus can promote chemical reactions that are difficult or impossible to achieve by conventional methods. In the present invention, a plasma generation apparatus is not specifically limited so long as it can generate non-thermal atmospheric pressure plasma. A carrier gas used to generate non-thermal atmospheric pressure plasma is not specifically limited and may be preferably one or more selected from the group consisting of oxygen, nitrogen, helium, and argon, more preferably nitrogen and/or argon.

In an embodiment of the present invention, "liquid plasma (non-thermal plasma treated solution, NTS)" is formed by generating high-density high-energy plasma in a liquid and may be prepared by exposing room-temperature non-thermal plasma (NTP) under atmospheric pressure. The term "liquid plasma" may be interchangeably used with "plasma-conditioned liquid material" or water plasma. The "liquid material" may be used without a specific limitation so long as it is a material in a liquid form, and may be preferably water, saline, buffer, or medium, most preferably medium.

Since the liquid plasma of the present invention can be supplied in the form of a liquid composition, it is convenient to distribute and carry the same. In addition, the liquid plasma can simultaneously provide moisturization and treatment to skin diseases where moisturization is important. Further, the liquid plasma causes less cell damage than direct plasma application to skin lesions, has no risk of skin damage such as burns due to incorrect operation of a user, and can be evenly applied to a wide and curved area.

In an embodiment of the present invention, "culture medium" refers to a medium that can support cell growth and survival in vitro, and includes all conventional media used in the art suitable for the culture of cells. Medium and culture conditions can be selected depending on the type of cells. A basal medium used for culturing of cells includes preferably a cell culture minimum medium (COMM) and generally, a carbon source, a nitrogen source, and trace elements. As examples of such a basal medium for cell culture, there are Dulbecco's Modified Eagle's Medium (DMEM), Minimal Essential Medium (MEM), Basal Medium Eagle (BME), RPMI1640, F-10, F-12, Glasgow's Minimal Essential Medium (GMEM), Iscove's Modified Dulbecco's Medium, and the like, but the present invention is not limited thereto.

In an embodiment of the present invention, "treatment" means any action that improves or advantageously alters the symptoms of a keloid or a consequent disease using the liquid plasma according to the present invention. Those skilled in the art to which the present application belongs, will be able to determine the exact criteria of keloid, and determine the degree of improvement and treatment with reference to the data presented by the Korean Medical Association.

In an embodiment of the present invention, "prevention" means any action that inhibits or delays the onset of keloids or other subsequent diseases using the liquid plasma according to the present invention. It will be apparent to those skilled in the art that the liquid plasma composition of the present invention having a therapeutic effect on keloid can be used to prevent keloid before the initial symptoms or symptoms of keloid appear.

In the present specification, "pharmaceutical composition" refers to a composition administered for a specific purpose. According to the purpose of the present invention, the pharmaceutical composition of the present invention includes a liquid plasma, which is prepared by irradiating a liquid material with plasma, as an effective ingredient and may include related proteins and a pharmaceutically acceptable carrier, excipient, or diluent. The "pharmaceutically acceptable" carrier or excipient means those that are approved by the governmental regulatory authority or listed in the government or other generally approved pharmacopoeia for use in vertebrates and more particularly in humans.

For parenteral administration, the pharmaceutical composition of the present invention may be in the form of a suspension, solution or emulsion in an oily or aqueous carrier, and may be prepared in the form of a solid or a semisolid. In addition, the pharmaceutical composition of the present invention may include a formulating agent such as a suspending agent, a stabilizer, a solubilizer, and/or a dispersant and may be sterilized. The pharmaceutical composition may be stabilized under production and storage conditions, and may be preserved against the contaminating action of microorganisms such as bacteria or fungi. Alternatively, the pharmaceutical composition of the present invention may be provided in a sterile powder form for reconstitution with a suitable carrier prior to use. The pharmaceutical composition may be provided in a unit-dose form or in a microneedle patch from, or may be contained in ampoules, in other unit-dose containers, or in multi-dose containers. Alternatively, the pharmaceutical composition may only be stored in a sterile liquid carrier, for example in a freeze-dried form that requires the addition of water for injection just before use. Immediately injectable solutions and suspensions may be prepared from sterile powders, granules, or tablets.

In some non-limiting embodiments, the pharmaceutical composition of the present invention may be formulated or included in the form of microspheres in a liquid. In certain non-limiting embodiments, the pharmaceutical composition of the present invention may include a pharmaceutically acceptable compound and/or mixture at a concentration of 0.001 to 100,000 U/kg. In addition, in certain non-limiting embodiments, a suitable excipient of the pharmaceutical composition of the present invention may include a preservative, a suspending agent, an additional stabilizer, a dye, a buffer, an antibacterial agent, an antifungal agent, and an isotonic agent, for example, sugar or sodium chloride. As used herein, the term "stabilizer" refers to a compound optionally included in the pharmaceutical composition of the present invention to increase shelf lifespan. In a non-limiting embodiment, a stabilizer may be a sugar, an amino acid, or a polymer. In addition, the pharmaceutical composition of the present invention may include one or more pharmaceutically acceptable carriers. The carrier may be a solvent or a dispersion medium. Non-limiting examples of a pharmaceutically acceptable carrier include water, saline, ethanol, polyols (e.g., glycerol, propylene glycol, and liquid polyethylene glycols), oils, and suitable mixtures thereof. Non-limiting examples of a sterilization technique applied to the pharmaceutical composition of the present invention include filtration through a bacteria-inhibiting filter, terminal sterilization, incorporation of sterile preparations, irradiation, sterile gas irradiation, heating, vacuum drying, and freeze drying.

In the present specification, "administration" means introducing the composition of the present invention to a patient in any suitable way, and the route of administration of the composition of the present invention may be any general route as long as it can reach a target tissue. The pharmaceutical composition of the present invention may be applied through oral administration, intraperitoneal administration, intravenous administration, intramuscular administration, subcutaneous administration, intradermal administration, intranasal administration, pulmonary administration, rectal administration, intraluminal administration, intraperitoneal administration, or intradural administration, and most preferably by applying to the skin or through subcutaneous or intradermal injection, but the present invention is not limited thereto.

A treatment method according to the present invention may include administrating the pharmaceutical composition in a pharmaceutically effective amount. An effective amount according to the present invention may be controlled depending upon various factors such as the type of disease, the severity of disease, effective ingredients contained in a composition, the types and amounts of other ingredients, the type of formulation, the age, weight, general health state, sex, and diet of a patient, administration time, administration route, a secretion rate of a composition, a treatment period, and concurrent drugs.

In an embodiment of the present invention, provided is a method of preparing a liquid plasma for preventing or treating keloids, the method including: (a) a step of charging a plasma generation apparatus with a carrier gas; (b) a step of supplying a voltage of 1 kV to 20 kV and a frequency of 10 to 30 kHz to the plasma generation apparatus to generate plasma; and (c) a step of irradiating a liquid material with the generated plasma, wherein the carrier gas in step (a) is one or more selected from a group consisting of nitrogen, helium, argon, and oxygen and is prepared by mixing nitrogen and argon in a ratio of 15:2% by volume, the irradiation of step (c) is carried out for 10 to 60 seconds per ml at a distance of 0.1 cm to 15 cm from a surface of a liquid material, and the liquid material of step (c) is water, saline, buffer, or medium.

In another embodiment of the present invention, provided is a pharmaceutical composition for preventing or treating keloids including a liquid plasma prepared according to any one of the methods, wherein the pharmaceutical composition is an oral formulation, a parenteral formulation, or a topical formulation and is used alone or in combination with surgery, radiation therapy, hormonal therapy, chemotherapy, and methods of using biological response modifiers.

In still another embodiment of the present invention, provided is a method of preventing or treating keloids, the method including a step of administering the pharmaceutical composition to a subject except for human.

Hereinafter, each step of the present invention will be described in detail.

Advantageous Effects

The present invention relates to a method of preventing or treating keloids using a liquid plasma. A liquid plasma according to the present invention is remarkably effective in inhibiting the generation and proliferation of keloids, thus being expected to be greatly utilized for the prevention and treatment of keloids.

BEST MODE

Hereinafter, the present invention will be described in more detail with reference to the following Examples. It will be apparent to those skilled in the art that Examples are merely for concretely explaining the invention and therefore, there is no intent to limit the invention to Examples.

EXAMPLE 1

Liquid Plasma (NTS) Preparation

Figure 1:
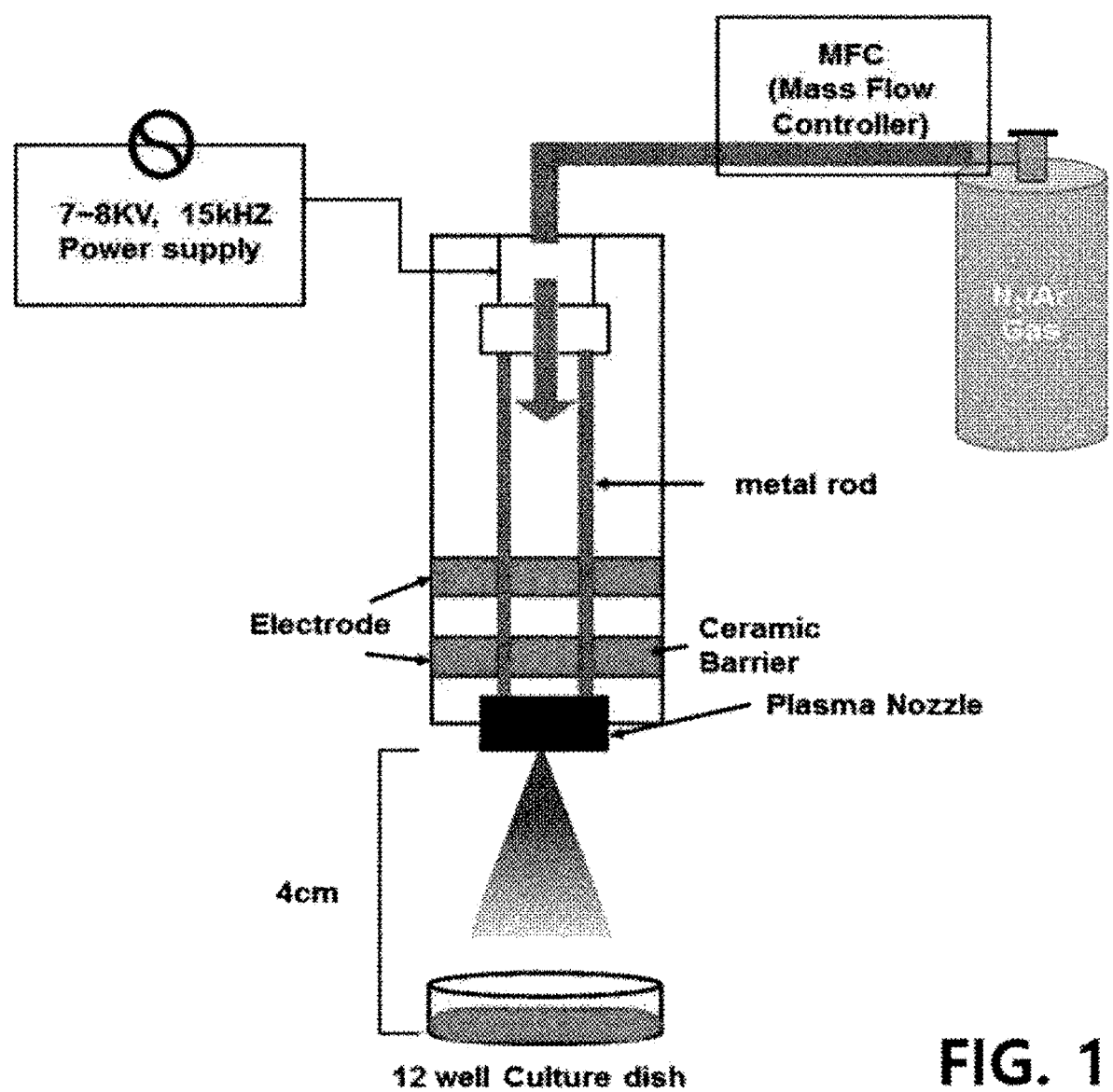
FIG. 1 is a schematic diagram illustrating a method of preparing a liquid plasma according to an embodiment of the present invention.

A liquid plasma was prepared using an atmospheric-pressure plasma generation apparatus including a quartz or ceramic tube, as a dielectric, and a non-thermal plasma source with multiple nozzles. The apparatus was provided with a gas supply nozzle with a diameter of less than 3 mm and was designed to generate uniform plasma of 1 inch size. A carrier gas was supplied at a flow rate of 10 L/min to the apparatus, and a bottom surface of a culture plate (12-well plate, TPP, Renner, Dannstadt, Germany) containing 2 ml of a cell medium was irradiated with plasma for 30 seconds per ml at a distance of 4 cm from the bottom surface. Here, a power supply of the plasma apparatus had specifications such as preferably a voltage of 1 to 20 kV and an average frequency 10 to 30 kHz, most preferably a voltage of 3 kV and an operation frequency of 25 kHz, but the present invention is not limited thereto. A schematic diagram of a method of preparing the liquid plasma is illustrated in FIG. 1.

EXAMPLE 2

Culture of Keloid Fibroblasts

Fibroblasts isolated from skin tissue, diagnosed as keloid, spread beyond an original wound boundary for one or more years even after a wounded skin tissue was recovered were termed "keloid fibroblasts (KF)." KF was cultured in RPMI-1640 medium containing 10% by volume of FBS and 1% by volume of an antibiotic/antimicrobial under 5% by volume of $CO_2$ in a 37° C. wet environment. Passage culture was performed when KF proliferated to a density of 80 to 90%. The passage was performed using trypsin. In examples of the present invention, cells of F2 to F7 generations were only used.

EXAMPLE 3

Confirmation of Nitric Oxide (NO) Generation Effect Upon Treatment of Keloid Fibroblasts with Plasma Primary keloid fibroblasts derived from humans were dispensed at a concentration of $1\times10^5$ cells/ml in a 96-well plate and stabilized for 24 hours, followed by treatment with plasma. Particularly, cells were directly treated with plasma (direct plasma) for 30 seconds using the plasma apparatus described in Example 1, or treated with a liquid plasma prepared according to the method of Example 1. The methods were classified and summarized in Table 1 according to the type of used gases.

TABLE 1

| | Direct plasma treatment | Non-thermal plasma treated solution (NTS) |
|---|---|---|
| Control | No treatment | Treatment with medium non-irradiated with plasma (general medium) |
| $N_2$ | | Use of nitrogen as carrier gas upon plasma generation |
| Ar | | Use of argon as carrier gas upon plasma generation |
| $N_2$/Ar | | Use of mixture of nitrogen and argon, mixed in ratio of 1500:200, as carrier gas upon plasma generation |

Figure 2:
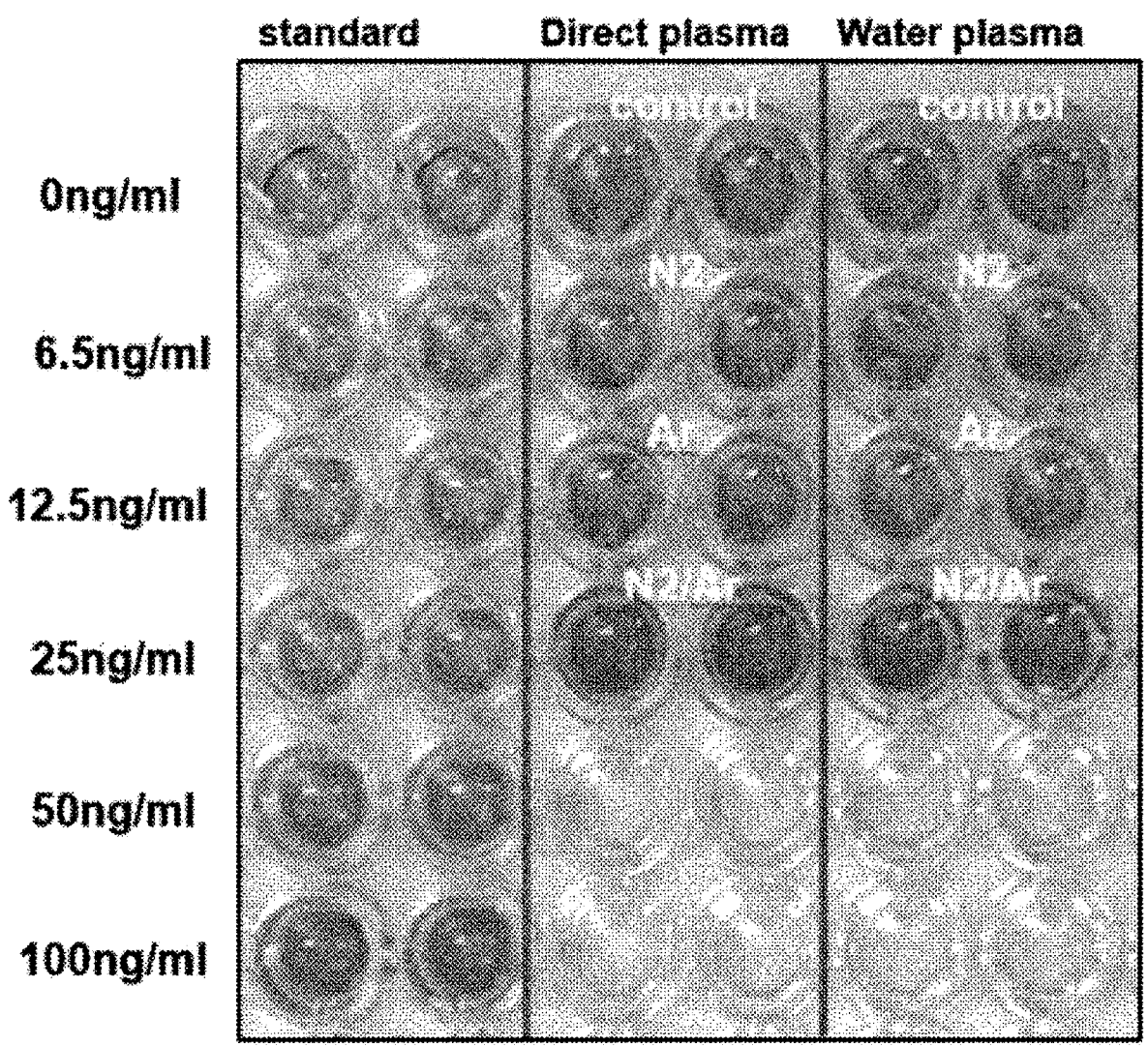
FIG. 2 is a result illustrating NO generation effects in keloid fibroblasts treated with a liquid plasma or directly treated with plasma using various carrier gases according to an embodiment of the present invention.

After treating with plasma or a liquid plasma, additional culturing was performed for 24 hours. The culture medium was collected and centrifuged (12,000 rpm, 3 min). Nitric oxide (NO) was quantified using the Griess reagent method. NO, generated from arginine (L-arginine) by a nitric oxide synthase, is known to play a role in promoting cellular metabolism through an increase in intracellular cGMP. In particular, 100 μl of a medium of each group and 100 μl of a Griess solution (5% (v/v) phosphoric acid containing 1% sulfanilamide and 0.1% naphthylethylenediamine) were dispensed in a 96-well plate and allowed to react for 10 minutes, followed by measuring an absorbance at 550 nm. Results are shown in FIG. 2.

From the experimental results, it was confirmed that ① a NO generation amount in the case treated with the liquid plasma was not reduced compared to the case in which cells were directly treated with plasma, ② both the case treated with the liquid plasma and the case directly treated with plasma exhibited NO generation increase effects compared to a control, and ③ NO generation increase effect in the case using the mixed nitrogen/argon gas as a carrier gas was more significant than the cases using nitrogen or argon alone.

EXAMPLE 4

Figure 3:
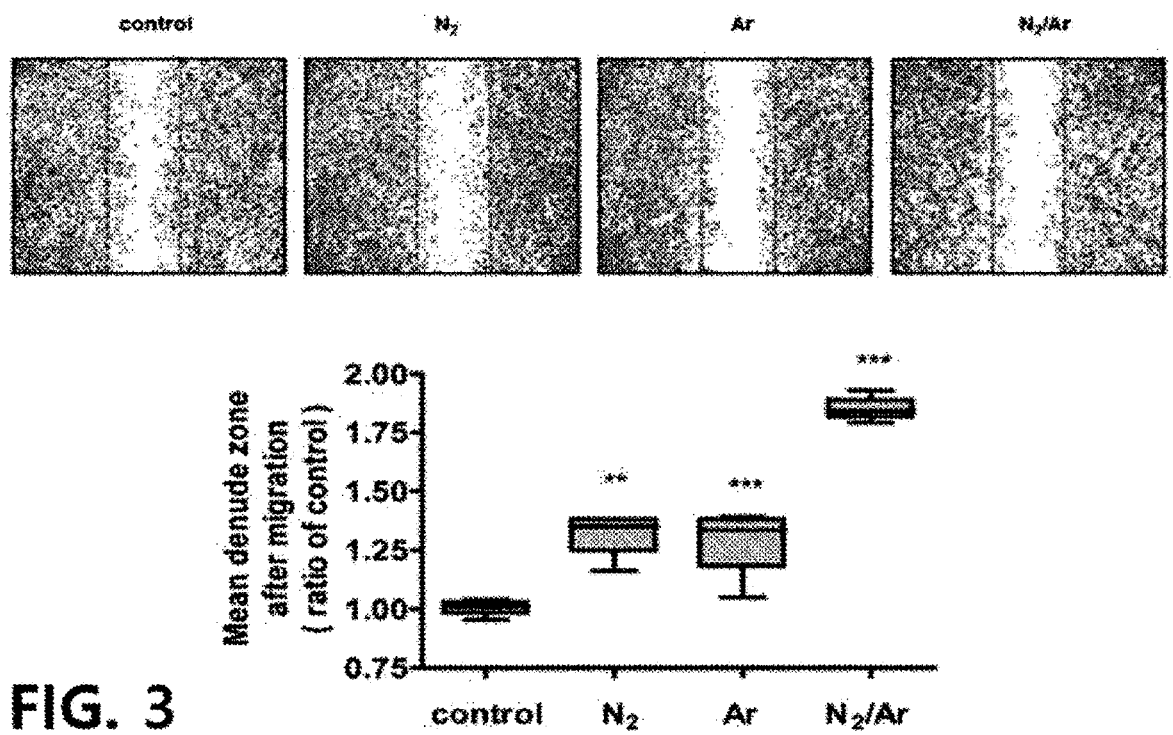
FIG. 3 is a result illustrating cell migration inhibition effect on keloid fibroblasts treated with a liquid plasma using various carrier gases according to an embodiment of the present invention.

Confirmation of Cell Migration Inhibition Effect Upon Treatment of Keloid Fibroblasts with Plasma To investigate the cell migration inhibition effect of keloid fibroblasts treated with a liquid plasma, the keloid fibroblasts were cultured at a density of 5×10$^5$/well in a 12-well culture plate. The center of cells forming a monolayer sheet was scraped with a tip, followed by washing to remove cell debris due to the scraping. Treatment with a liquid plasma was performed as summarized in Table 1. After performing additional culture for 24 hours, cellular migration was measured. Results are shown in FIG. 3.

As an experimental result, it was confirmed that all groups treated with the liquid plasma exhibited significant inhibition of cell migration, particularly the case using the mixed nitrogen/argon gas as a carrier gas exhibited greatly significant cell migration effect, compared to the control treated with a general medium.

EXAMPLE 5

Confirmation of Plasma Treatment Time-Dependent Cell Migration Inhibition Effect in Keloid Fibroblasts Based on the experimental results of Example 4, cell migration inhibition effects of liquid plasmas prepared using the mixed nitrogen/argon gas as a carrier gas, but varying a plasma treatment time were investigated. Experiments were investigated in the same manner as in Example 4.

Figure 4:
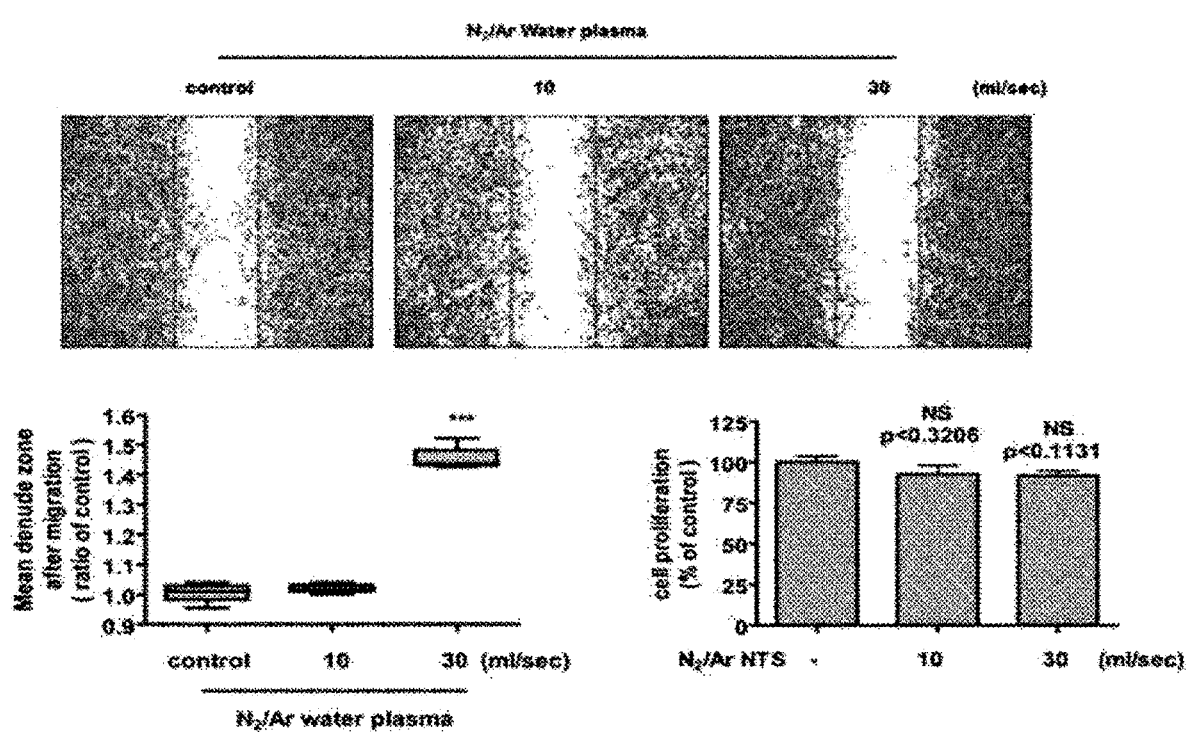
FIG. 4 is a result illustrating cell migration inhibition effects on keloid fibroblasts treated with liquid plasmas prepared using various plasma treatment times according to an embodiment of the present invention.

As experimental results, it was confirmed that the cell migration inhibition effect on keloid fibroblasts was slight in the case of the liquid plasma prepared by irradiating a medium with plasma for 10 seconds, whereas the cell migration inhibition effect on keloid fibroblasts in the case of the liquid plasma prepared by irradiating a medium with plasma for 30 seconds was significant, compared to the control (general medium). However, cell proliferation was similarly maintained in all groups, which indicates that the cell migration inhibition is not due to a decrease in cell proliferation. Results are shown in FIG. 4.

From the results of Examples 1 to 5, it was confirmed that, when plasma was applied in the form of a liquid plasma, the therapeutic effect on keloids was not reduced, compared to the case wherein cells were directly treated with plasma. However, considering that, when treated with a liquid plasma, cell damage is reduced, there is no risk of skin damage such as burns due to a wrong apparatus operation by a user, and plasma may be uniformly applied even to a wide and curved area, compared to the case of directly treating a wounded skin lesion with plasma, a liquid plasma is more medically useful than direct plasma treatment.

In addition, it was confirmed that therapeutic effects differed depending upon the type of carrier gas used to generate plasma, and, when plasma was generated using mixed nitrogen/argon gas as a carrier gas, treatment effects on keloids were superior to the cases of using a nitrogen or argon gas alone.

The invention claimed is:

1. A method of preparing a liquid plasma for preventing or treating keloids, the method comprising:
   (a) a step of charging a plasma generation apparatus with a carrier gas, wherein the carrier gas is prepared by mixing nitrogen and argon at a ratio of 15:2% by volume;
   (b) a step of supplying a voltage of 1 kV to 20 kV and a frequency of 10 to 30 kHz to the plasma generation apparatus to generate plasma; and
   (c) a step of irradiating a liquid material with the generated plasma, wherein the irradiation is carried out for 10 to 60 seconds per ml at a distance of 0.1 cm to 15 cm from a surface of a liquid material,
   wherein the liquid material of step (c) is water, saline, buffer, or medium.

2. A pharmaceutical composition, comprising a liquid plasma prepared according to the method according to claim 1.

3. The pharmaceutical composition according to claim 2, wherein the pharmaceutical composition is an oral formulation, a parenteral formulation, or a topical formulation.

4. The pharmaceutical composition according to claim 2, wherein the pharmaceutical composition is used alone or in combination surgery, radiation therapy, hormonal therapy, chemotherapy, and methods of using biological response modifiers.

5. A method of preventing or treating keloids, the method comprising a step of administering the pharmaceutical composition according to claim 2 to a subject.

\* \* \* \* \*